United States Patent
Kilburn-Peterson et al.

(10) Patent No.: US 8,523,903 B2
(45) Date of Patent: Sep. 3, 2013

(54) PARTIAL THICKNESS ROTATOR CUFF REPAIR SYSTEM AND METHOD

(75) Inventors: Christopher Kilburn-Peterson, Raynham, MA (US); Jose E. Lizardi, Raynham, MA (US); Kristian DiMatteo, Raynham, MA (US)

(73) Assignee: DePuy Mitek, LLC, Raynham, MA (US)

(*) Notice: Subject to any disclaimer, the term of this patent is extended or adjusted under 35 U.S.C. 154(b) by 265 days.

(21) Appl. No.: 12/908,261

(22) Filed: Oct. 20, 2010

(65) Prior Publication Data
US 2011/0270308 A1 Nov. 3, 2011

Related U.S. Application Data

(60) Provisional application No. 61/256,362, filed on Oct. 30, 2009.

(51) Int. Cl.
*A61B 17/04* (2006.01)

(52) U.S. Cl.
USPC .......................... 606/232; 606/148

(58) Field of Classification Search
USPC ............... 606/60, 104, 139, 148, 150, 232, 606/300, 301, 304, 305, 309, 318, 319, 323, 606/325, 916; 623/13.11, 13.14; 128/898
See application file for complete search history.

(56) References Cited

U.S. PATENT DOCUMENTS

| | | | |
|---|---|---|---|
| 5,441,502 A | 8/1995 | Bartlett | |
| 5,948,000 A | 9/1999 | Larsen | |
| 5,948,001 A | 9/1999 | Larsen | |
| 6,406,479 B1 | 6/2002 | Justin | |
| 6,616,665 B2 | 9/2003 | Grafton | |
| 2002/0183762 A1* | 12/2002 | Anderson et al. | 606/104 |
| 2003/0130694 A1 | 7/2003 | Bojarski | |
| 2004/0073227 A1 | 4/2004 | Dreyfuss | |
| 2006/0247641 A1* | 11/2006 | Re et al. | 606/72 |
| 2007/0015953 A1* | 1/2007 | MacLean | 600/31 |
| 2008/0058816 A1 | 3/2008 | Philippon | |
| 2010/0292731 A1* | 11/2010 | Gittings et al. | 606/232 |
| 2010/0318139 A1* | 12/2010 | Beauchamp | 606/86 R |

FOREIGN PATENT DOCUMENTS

WO WO 2010/132310 A1 11/2010

OTHER PUBLICATIONS

EP Search Report dated May 16, 2011 for EP Appl. No. 10251881.8.
Millstein, Eric S. et al., Arthroscopic Management of Partial, Full-Thickness, and Complex Rotator Cuff Tears: Indication, Techniques, and Complications, Arthroscopy: The Journal of Arthroscopic and Related Surgery, Dec. 2003, pp. 189-199, vol. 19, No. 10.

(Continued)

*Primary Examiner* — Corrine M McDermott
*Assistant Examiner* — Robert A Lynch

(57) ABSTRACT

A method and system is provided for of attaching a rotator cuff tendon to its associated humeral head. The method includes the steps of passing a positional guide through the tendon toward the humeral head at a target site and positioning a suture anchor between the humeral head and the tendon at the target site by passing the suture anchor under the tendon. The suture anchor is driven into the humeral head and suture is passed from the suture anchor and through the tendon to attach the tendon to the humeral head at the target site.

6 Claims, 11 Drawing Sheets

(56) References Cited

OTHER PUBLICATIONS

Waibl, Bernhard et al., Partial-Thickness Articular Surface Supraspinatus Tears: A New Transtendon Suture Technique, Arthroscopy: The Journal of Arthroscopic and Related Surger, Mar. 2005, pp. 376-381, vol. 21, No. 3.

Lo, Ian K.Y., et al., Transtendon Arthroscopic Repair of Partial-Thickness, Articular Surface Tears of the Rotator Cuff, Arthroscopy: The Journal of Arthroscopic and Related Surgery, Feb. 2004, pp. 214-220, vol. 20, No. 2.

Fox, Jeff A. et al., Pasta Lesion-Trans-Tendon Technique for Repair, Operative Techniques in Orthopaedics, 2002, pp. 191-196, vol. 12, No. 3.

Porat, Sharoun et al., Repair of partial thickness rotator cuff tears: A retrospective review with minimum two-year follow-up, J Shoulder Elbow Surg, 2008, pp. 727-721, vol. 17, No. 5.

Gonzalez-Lomas, Guillem et al., In situ transtendon repair outperforms tear completion and repair for partial articular-sided supraspinatus tendon tears, J Shoulder Elbow Surg, Sep./Oct. 2008, pp. 722-728, vol. 17, No. 5.

Brockmeier, Stephen F. et al., Arthroscopic Intratendinous Repair of the Delaminated Partial-Thickness Rotator Cuff Tear in Overhead Athletes, Arthroscopy: The Journal of Arthroscopic and Related Surgery, Aug. 2008, pp. 961-965, vol. 24, No. 8.

\* cited by examiner

PARTIAL THICKNESS ROTATOR CUFF REPAIR SYSTEM AND METHOD

BACKGROUND

The present application relates to systems and methods for performing a repair of a partial thickness rotator cuff tear.

A PASTA (partial articular surface tendon avulsion) lesion in a rotator cuff of a shoulder can be particularly difficult to repair. The rotator cuff comprises a group of muscles which surround the shoulder and tendons which attach those muscles to the humeral head. The tendons have a footprint where they attach to the humeral head and in a PASTA lesion a portion of the tendon's footprint becomes detached from the humeral head. Such lesions are most commonly found on the supraspinatus tendon.

One option for treatment is completion of the tear and repair using standard techniques for a full thickness tear. Preservation of the existing attachment is thus lost and the entire tendon must be reattached. Another option comprises passing a suture anchor through the tendon and into the humeral head, passing suture through the tendon and tying down the tendon to effect reattachment. This causes further trauma to the tendon.

SUMMARY OF THE INVENTION

The present invention provides systems and methods for repairing a PASTA lesion which provides advantages over current treatment options.

A method, according to the present invention, provides for attaching a partially torn rotator cuff tendon to its associated humeral head. The method comprises the steps of: passing a positional guide through the tendon toward the humeral head at a target site; positioning a suture anchor between the humeral head and the tendon at the target site by passing the suture anchor laterally under the tendon; driving the suture anchor into the humeral head; and passing suture from the suture anchor and through the tendon to attach the tendon to the humeral head at the target site.

Preferably, the positional guide is a needle.

In one aspect of the invention, the step of driving the suture anchor into the humeral head comprises rotating the suture anchor via a tool inserted laterally between the tendon and the humeral head. The tool could employ a ratchet drive.

In another aspect of the invention, the step of driving the suture anchor comprises passing a driver over the positional guide and through the tendon to engage the suture anchor. The suture anchor can be threaded such that the driver rotates the suture anchor into the humeral head, or the driver can merely push or mallet the suture anchor into the humeral head.

In one aspect of the invention, the suture anchor comprises a first portion and a second portion which can assemble with each other and wherein the step of positioning the suture anchor at the target site comprises the steps of passing the first portion and the second portion in a disassembled state laterally under the tendon and then assembling the first portion to the second portion around the positional guide. Preferably, the positional guide is engaged with the humeral head during the step of assembling the first portion to the second portion.

Preferably, the step of passing an awl head laterally under the tendon to the target site and engaging the awl head against the humeral head via the positional guide. The awl head can then be driven into the humeral head to create a bone hole. Preferably, the positional guide comprises a threaded distal tip and the step of driving the awl head into the humeral head comprises engaging the awl head with the threaded distal tip of the positional guide, impacting the awl head via the positional guide to create the bone hole and then disengaging the awl head from the positional guide by unthreading the positional guide therefrom. Then the suture anchor can be driven into the humeral head comprises inserting the suture anchor into the bone hole.

One aspect of the invention involves inserting an inner portion into the suture anchor, the inner portion passing through the tendon and into a recess in the suture anchor and engaging it therein. Preferably, the inner portion has at least one suture attached thereto.

A suture anchor kit according to the present invention comprises a suture anchor having at least one suture limb extending therefrom, a distal end for entering bone, an opposite proximal end and a side between the distal end and proximal end. A suture anchor passing tool is adapted to grasp the suture anchor side.

Preferably the passing tool has a height adjacent the suture anchor and over a length thereof sufficient to pass the suture anchor under a tendon in a rotator cuff and wherein the height is less than a length of the suture anchor between its distal end and proximal end.

In one aspect of the invention the suture anchor has an aperture in its side and the tool has a distal tip sized to fit within the aperture whereby to grasp the anchor.

Preferably the suture anchor kit according further comprises instructions for use which include an instruction to pass the suture anchor under a tendon in a rotator cuff.

A suture anchor kit according to the present invention comprises a positional guide adapted to pass through a rotator cuff tendon, a suture anchor, a driver adapted to drive the suture anchor into the humeral head; and instructions for positioning the suture anchor a target site by passing the suture anchor laterally underneath a rotator cuff tendon to intercept the positional guide which is passed through the rotator cuff tendon.

A suture anchor kit according to the present invention comprises a positional guide adapted to pass through a rotator cuff tendon, a suture anchor, a driver adapted to drive the suture anchor into the humeral head, and wherein the driver engages laterally with the suture anchor whereby to allow the suture anchor and the driver to be placed at a target site under a rotator cuff tendon by passing them laterally underneath the rotator cuff tendon. The driver can comprise a ratchet mechanism. The driver can also comprise a powered rotational drive head adapted to rotate the suture anchor about a central axis thereof.

A suture anchor kit according to the present invention comprises a positional guide adapted to pass through a rotator cuff tendon, a suture anchor having a central bore through a central axis thereof, the bore being open laterally whereby to be engageable laterally with the positional guide at a target site beneath the rotator cuff tendon; and a driver adapted to drive the suture anchor into the humeral head.

The suture anchor can comprises a first lateral portion and a second lateral portion, the first lateral portion and second lateral portion engageable with each other laterally at a target site beneath a rotator cuff tendon with the positional guide within the central bore.

A suture anchor kit according to the present invention comprises a longitudinally extended positional guide having a sharp distal tip adapted to pass through a rotator cuff tendon, an awl head threadably engageable with the distal tip of the positional guide and adapted to form a bone hole in a humeral head, a suture anchor, and a driver adapted to insert the suture anchor into the bone hole.

Preferably a manipulator is provided which is engagable laterally with at least one of the suture anchor and awl, whereby to allow insertion thereof underneath the rotator cuff tendon. Preferably, a suture extends from the anchor and a suture engaging notch is provided in one of the driver or the positional guide whereby to allow capture of the suture in the suture engaging notch and passage of the suture through the rotator cuff tendon.

DETAILED DESCRIPTION

Figure 1:
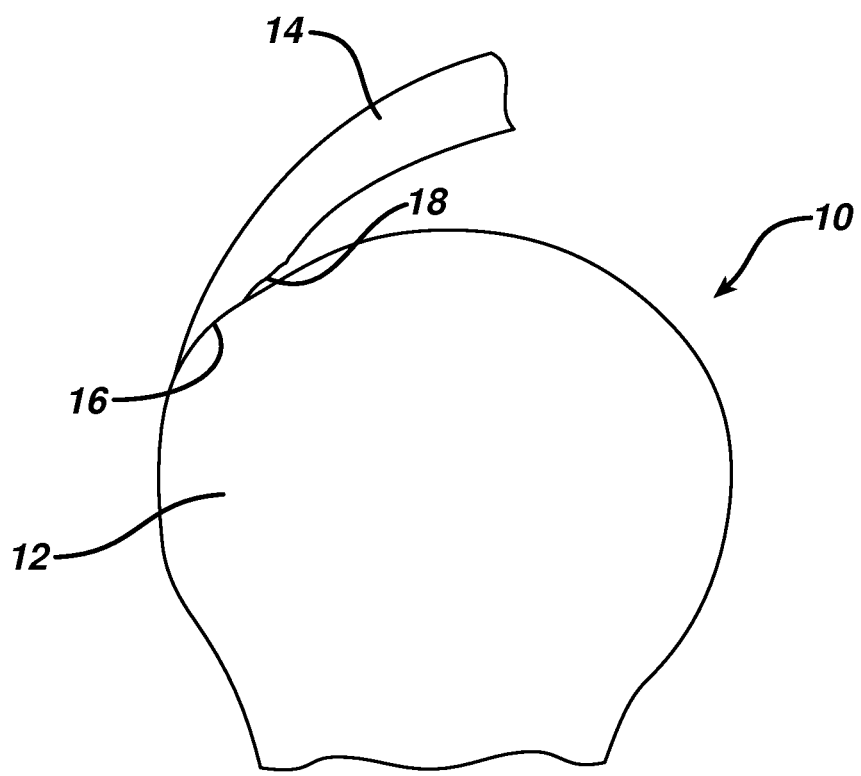
FIG. 1 is a side elevation view of a humerus and a tendon of the rotator cuff showing a PASTA lesion.

FIG. 1 depicts a humerus 10 having a humeral head 12 and a tendon 14 attached to the humeral head 12. The tendon 14 has a footprint 16 where it attaches to the humeral head 12 and it can be seen that a portion 18 of the footprint 16 has come detached. The space between the tendon 14 and the humeral head 12 is exaggerated for clarity.

Figure 2:
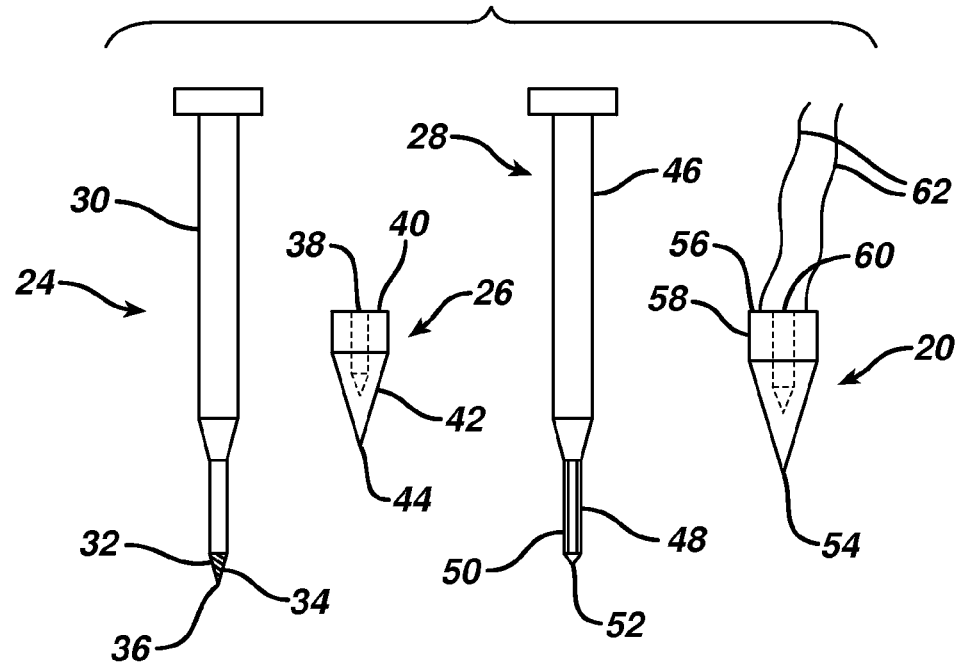
FIG. 2 is a side elevation view of an instrument set according to the present invention.

FIG. 2 depicts and a suture anchor 20 and instruments 22 for placement of the suture anchor 20 into the humeral head 12 beneath the detached portion 18 of the tendon footprint 16. The instruments 22 include a first driver 24, an awl head 26 and a second driver 28. The first driver 24 has an elongated shaft 30 and terminates at its distal end 32 with threads 34 and a sharp point 36. The awl head 26 has a threaded opening 38 at its proximal end 40 and a conical section 42 at its distal end 44. The threads 34 of the first driver 24 mate with the threaded opening 38 of the awl head 26. The second driver 28 comprises an elongated shaft 46 and near its distal end 48 has a hexagonal cross section 50 and terminates in a sharp point 52. The suture anchor 20 has a distal end 54, proximal end 56, a threaded outer surface 58 and a hexagonal opening 60 at its proximal end 56 which mates with the hexagonal portion 50 of the second driver 28. A pair of sutures 62 extend from the suture anchor 20.

Figure 3:
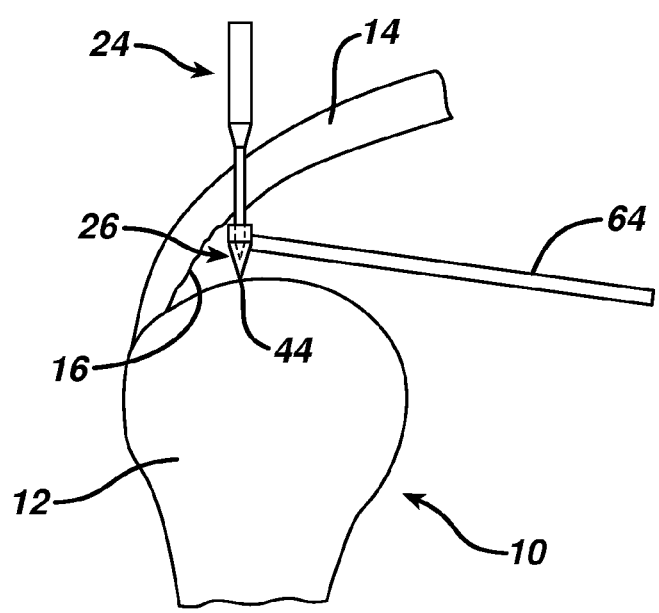
FIG. 3 is a side elevation view of the humerus of FIG. 1 and showing a step in a procedure according to the present invention in which an awl of FIG. 2 is positioned underneath the tendon and a first driver of FIG. 2 is passed through the tendon to engage the awl.
Figure 4:
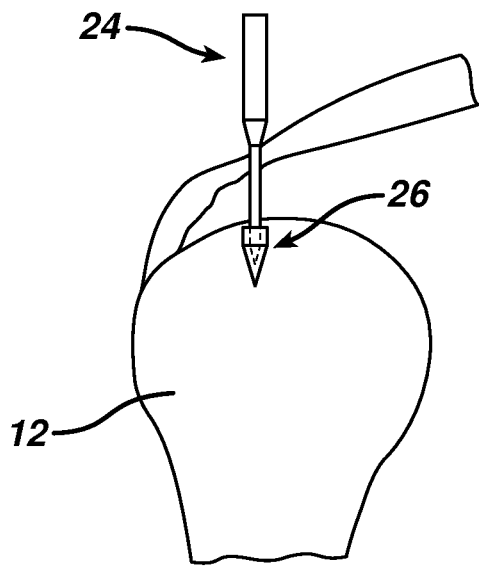
FIG. 4 is a side elevation view of the procedure of FIG. 3 showing the awl creating a bone hole in the humerus beneath the tendon.
Figure 5:
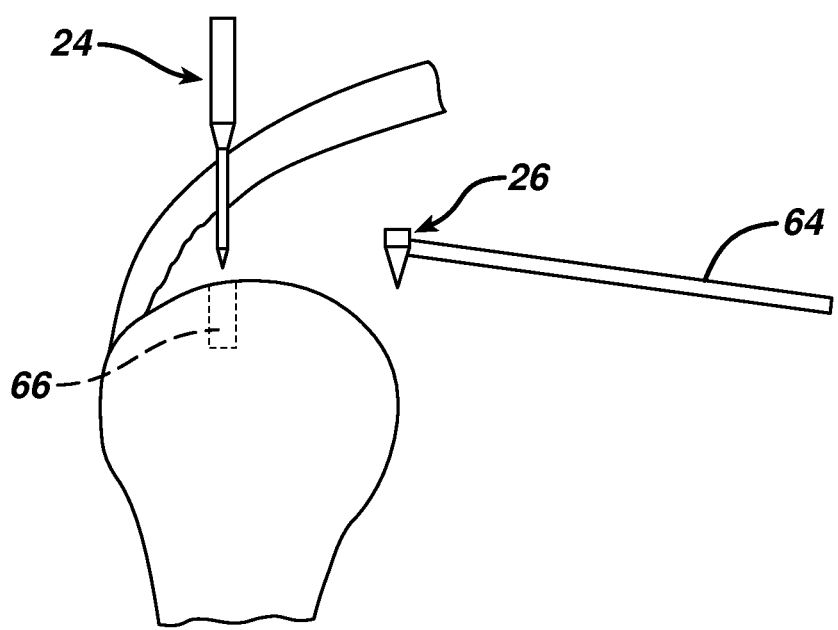
FIG. 5 is a side elevation view of the procedure of FIG. 3 showing the bone hole and showing awl and first driver being removed from the site.
Figure 6:
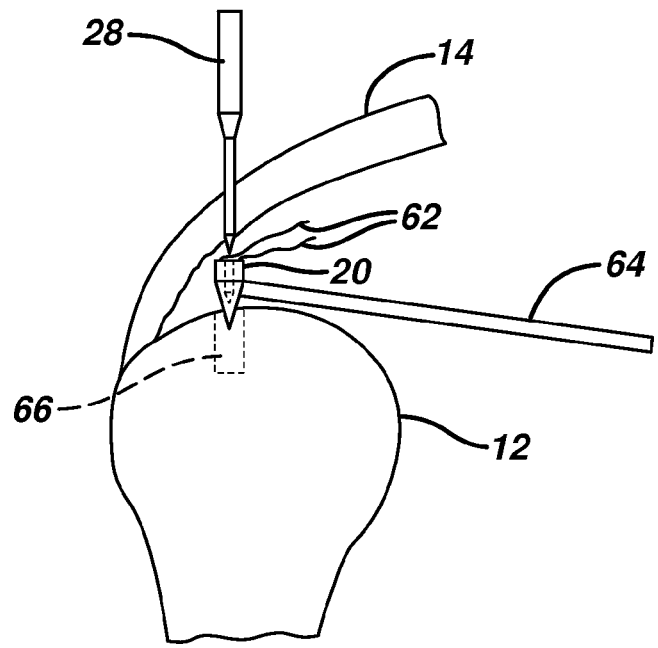
FIG. 6 is a side elevation view of the procedure of FIG. 3 showing a suture anchor of FIG. 2 being positioned beneath the tendon at the bone hole and a second driver of FIG. 2 being passed through the tendon to engage the suture anchor.
Figure 7:
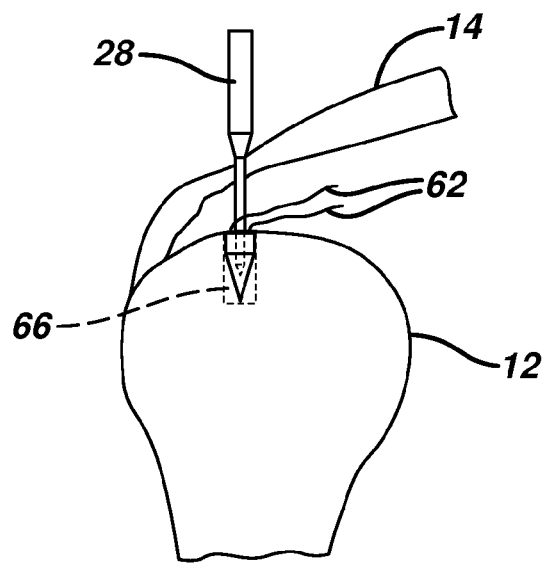
FIG. 7 is a side elevation view of the procedure of FIG. 3 showing the anchor being driven into the bone hole.
Figure 8:
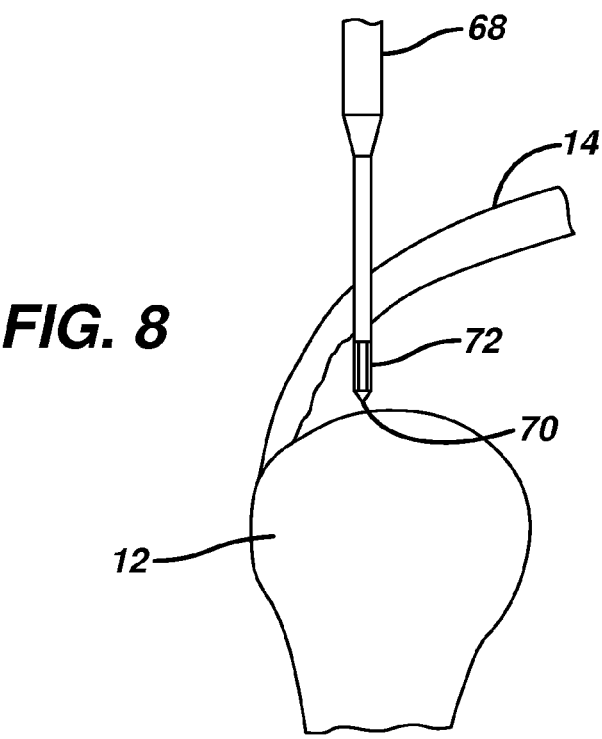
FIG. 8 is a side elevation view of a humerus and a second embodiment of an instrument set and procedure according to the present invention, wherein an awl is passed through the tendon.
Figure 9:
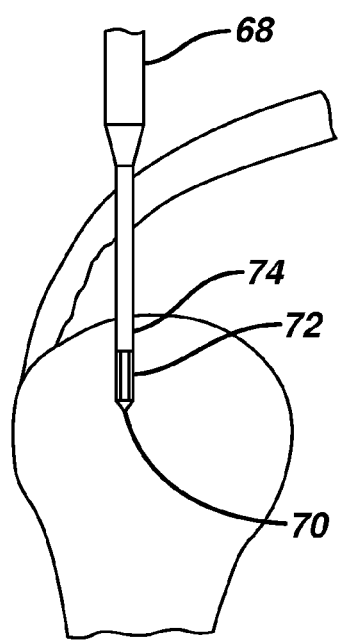
FIG. 9 is a side elevation view of the procedure of FIG. 8 showing the awl tapping a bone hole in the humerus beneath the tendon.
Figure 10:
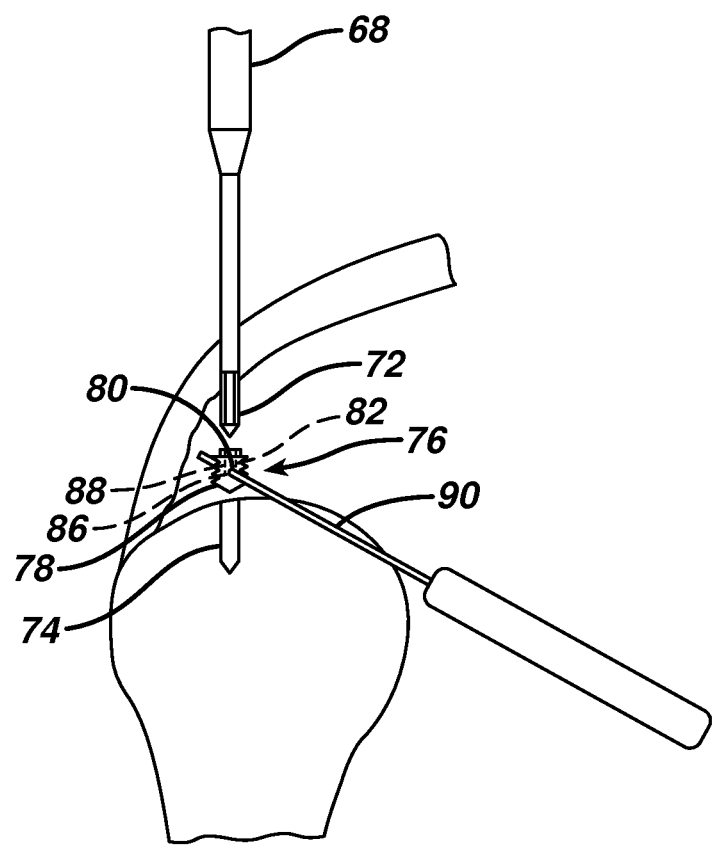
FIG. 10 is a side elevation view of the procedure of FIG. 8 showing an outer body of a suture anchor being passed beneath the tendon to the bone hole.
Figure 11:
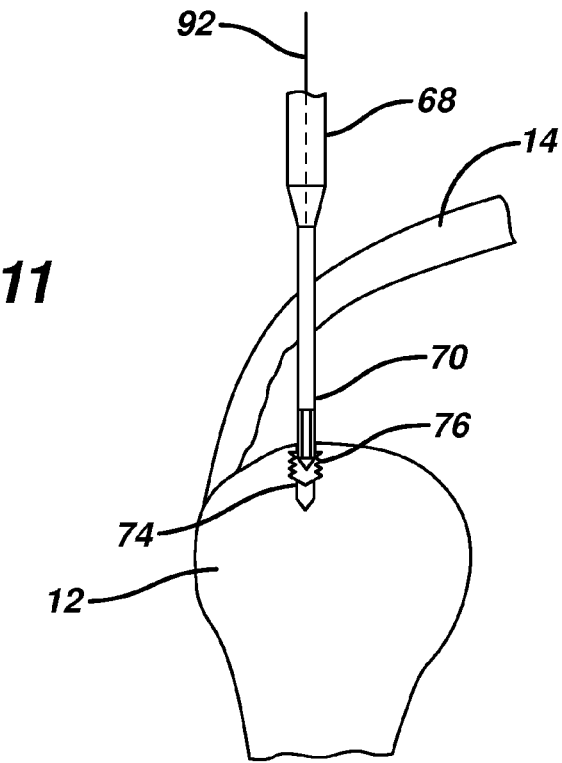
FIG. 11 is a side elevation view of the procedure of FIG. 8 showing the outer body being driven into the bone hole.
Figure 12:
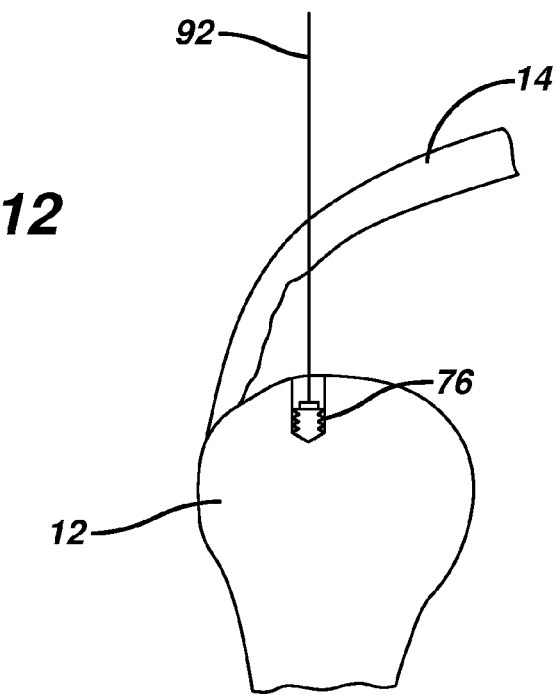
FIG. 12 is a side elevation view of the procedure of FIG. 8 showing the outer body positioned in the bone hole with a guide wire passing out through the tendon.
Figure 13:
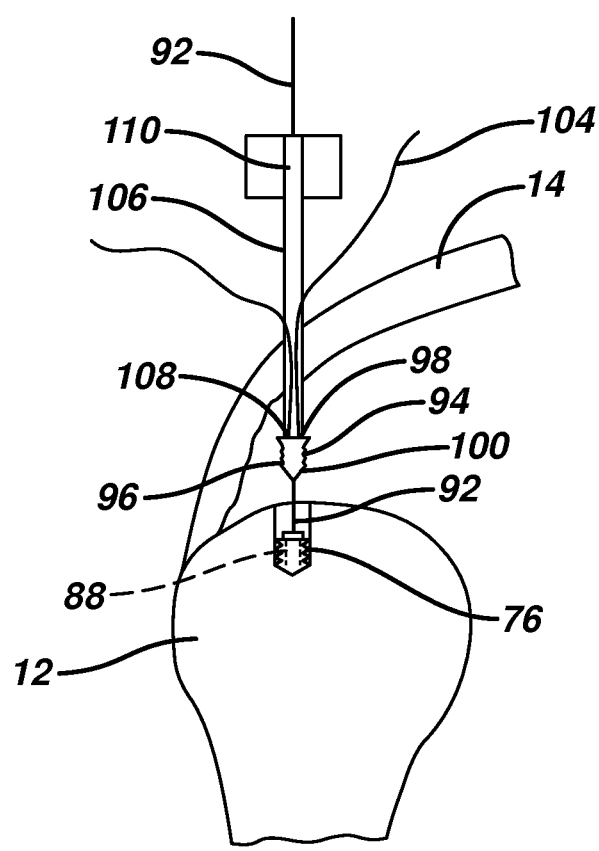
FIG. 13 is a side elevation view of the procedure of FIG. 8 showing an inner body of the suture anchor having a pair of suture limbs extending therefrom and a cannulated driver therefor being passed down the guide wire to engage the inner body.

Turning also now to FIGS. 3 to 7, to effect a repair a surgeon inserts the point 36 of the first driver 24 through the tendon 14 and locates the point 36 at a location on the humeral head 12 at which the surgeon desires to implant the suture anchor 20. The point 36 is malleted slightly into the humeral head 12 to make a defect. A small amount of biocompatible dye can be carried by the point 36 which is then transferred to the bone during malleting to ease later finding the defect visually. Then as depicted in FIG. 3 specifically a grasper 64 having the awl head 26 attached thereto is inserted under the tendon 14 and the awl head distal end 44 is placed into the defect made by the first driver 24. The first driver 24 is threaded into the awl head 26 and the grasper 64 is removed. The awl head 26 is then malleted into the humeral head 12 via the first driver 24 (see specifically FIG. 4) to create a hole 66 for receipt of the suture anchor 20. The awl head 26 is then held by the grasper 64, detached from the first driver 24 and removed (see specifically FIG. 5).

Now that the hole 66 has been prepared the suture anchor 20 is passed under the tendon 14 and position at the hole 66 via the grasper 64. The second driver 28 is passed through the tendon 14, preferably through the same location as which the first driver was passed, and engages the suture anchor 20 (see specifically FIG. 6). The anchor 20 is then driven into the hole 66 via the second driver 28. Completion of the repair can then be affected now that an anchor 20 is successfully located beneath the tendon 14. For instance, the sutures 62 can be passed through the tendon 14 in different locations via a suture grasper (not shown) and then tensioned and knotted above the tendon 14 to hold the tendon 14 against the humeral head 12.

Preferably each of the drivers 24 and 28 are of the minimum diameter necessary for strength such that minimal damage is caused to the tendon 14 as they are passed therethrough. Preferably they have diameters, at least of the portion passing through the tendon 14, of less than 4 mm and more preferably less than 3 mm. In an alternate embodiment not shown, the features (namely the threads 34 and hexagonal cross section 50) of the first and second drivers 24 and 28 are combined into a single driver so only one pass need be made through the tendon 14. The suture anchor 20 can be formed of any biocompatible material such as stainless steel or a bioabsorbable polymer. The HEALIX BR dual threaded suture anchor in BIOCRYL RAPIDE available from DePuy Mitek, Inc. of Raynham, Mass. BIOCRYL RAPIDE is a bioabsorbable polymer formed of homogenous blend of TriCalcium Phosphate (TCP) and Polylactic/polyglycolic Acid (PLGA). Although, a threaded anchor 20 is disclosed the invention is not so limited and other anchor types, such as a push-in anchor, could also be employed.

Turning now to FIGS. 8 to 13 which illustrate an alternative embodiment of the invention, an awl 68 having a sharp distal tip 70 and a hexagonal cross section 72 proximal thereof penetrates the tendon 14 and is malleted into the humeral head 12 to form a pilot hole 74. An anchor outer body 76 has external threads 78, a lateral aperture 80 and an axial opening 82 at a proximal end 84 of the anchor outer body 76. The axial opening has a distal hexagonal section 86 which mates with the hexagonal cross section 72 of the awl 68 and also has a proximal threaded portion 88. The anchor out body 76 is passed under the tendon 14 via a passing stick 90 inserted through the lateral aperture 80 and the awl 68 is then engaged to the anchor outer body 76 via the hexagonal section 86. With the passing stick 90 removed, the awl is used to drive the anchor outer body 76 into the humeral head 12 at the pilot hole 74. A guide wire 92 is left extending out of the anchor body and is withdrawn through the tendon 14 as the awl 68 is removed. It is preferably held in the anchor body by friction to allow easy removal later during the procedure. A cannulated inner anchor 94 can then be passed down over the guidewire 92 to engage the threaded portion 88 of the anchor outer body 76. The inner anchor 94 comprises a threaded outer surface 96, a hexagonal proximal opening 98, an axial cannulation 100 for receiving the guide wire 92, a suture attachment 102 and a pair of suture ends 104 extending therefrom. The inner anchor 94 is loaded onto a driver 106 having a distal hexagonal portion 108 and a cannulation 110 for receiving the guide wire 92. The guide wire 92 is threaded into the cannulations 100 and 110 and the inner anchor 94 is passed down the guide wire 92 to mate with the threaded section 88 of the anchor outer body 76. Although the connection between the inner anchor 94 and outer body 76 is shown as threaded, other connection types are possible as for instance a snap-fit with radially extending barbs on the inner anchor 94 engaging a lip on the outer body 76 to prevent proximal withdrawal of the inner anchor 94. The driver 106 and guide wire 92 are then removed leaving the inner anchor 94 affixed to the humeral head 12 beneath the tendon 14 with the pair of suture ends 104 passing through the tendon 14.

Figure 14:
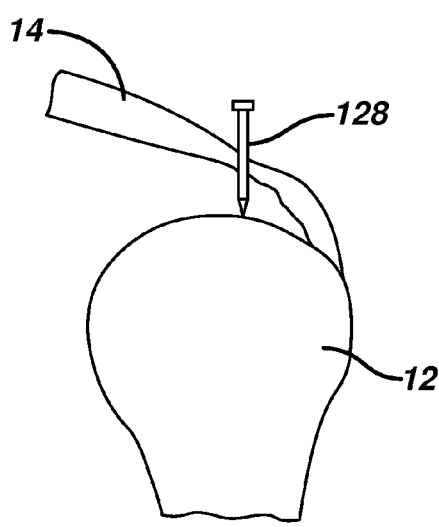
FIG. 14 is a perspective view of a humerus and a third embodiment of an instrument set and procedure according to the present invention, wherein a spinal needle has been passed through the tendon to a desired location of placing a suture anchor.
Figure 15A:
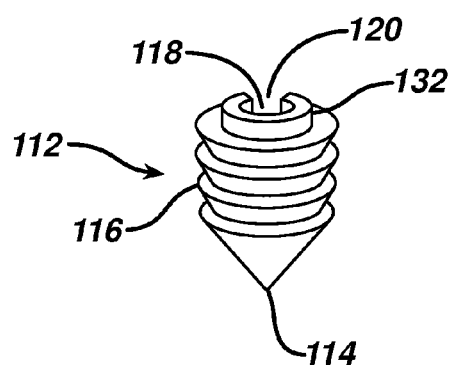
FIG. 15 is a perspective view of a suture anchor having a side slot for the procedure of FIG. 14 and a holding tool for the suture anchor.
Figure 15B:
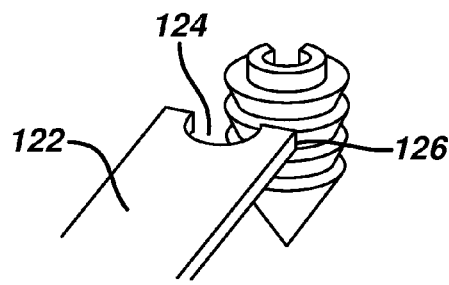
Figure 16:
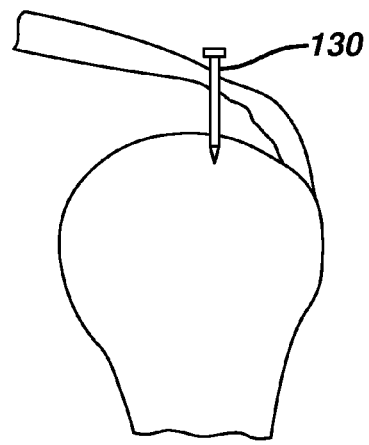
FIG. 16 is a perspective view of the procedure of FIG. 14 showing the suture anchor being passed beneath the tendon.

FIGS. 14 to 16 illustrate a further embodiment of the invention in which a push-in anchor 112 comprises a sharp distal tip 114, barbed exterior ridges 116 for enhanced fixation in bone, and an axial cannulation 118 which has a full length side opening 120. A grasper 122 has a semi-circular cut-out 124 at its distal end 126 adapted to snap fit with the anchor 112. To effect a repair of a PASTA lesion a surgeon places a needle 128, such as a spinal needle, through the tendon 14 and engages the humeral head 12 at a desired location for placement of the anchor 112. The anchor 112, via the grasper 122, is slid under the tendon 14 and adjusted to engage the needle 128 in the cannulation 118 through its side opening 120. The opening 120 can be sized to effect a snap-fit of the anchor 112 to the needle 128. A cannulated driver 130 is then passed down over the needle 128 to engage the anchor 112 at its proximal end 132 so that the anchor 112 can be malleted into the humeral head 12.

Figure 17:
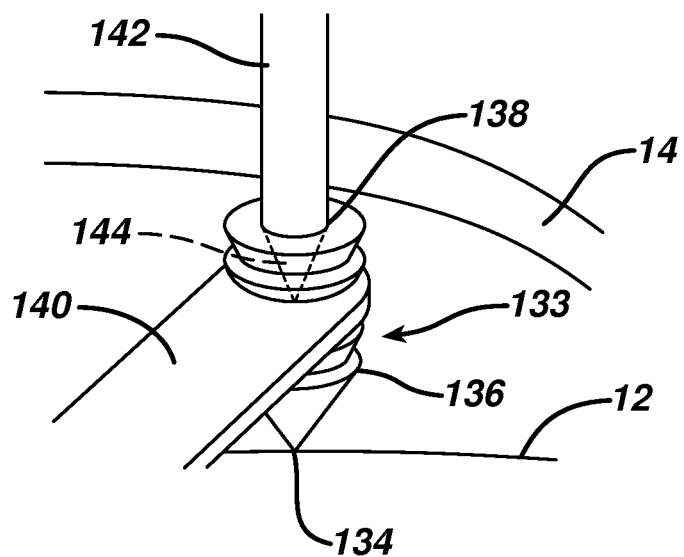
FIG. 17 is a perspective view of a humerus and a fourth embodiment of an instrument set and procedure according to the present invention showing a suture anchor which has been passed under the tendon being driven into the humerus via a driver passed through the tendon.

FIG. 17 illustrates a similar embodiment in which a push-in anchor 133, having a sharp distal tip 134, barbed ridges 136 and a proximal tool receiving opening 138 is manipulated with a grasper 140 similar to the grasper 122. Here, a driver 142 has a sharp distal tip 144 which is first used to punch a small pilot hole into the humeral head 12 at the desired location for placing the anchor 132. Then the anchor 132 is slid under the tendon 14 and positioned with its tip 134 in the hole. The driver tip 144 engages the opening 138 in the anchor 132 and the anchor 132 is then malleted into the humeral head 12.

Figure 18:
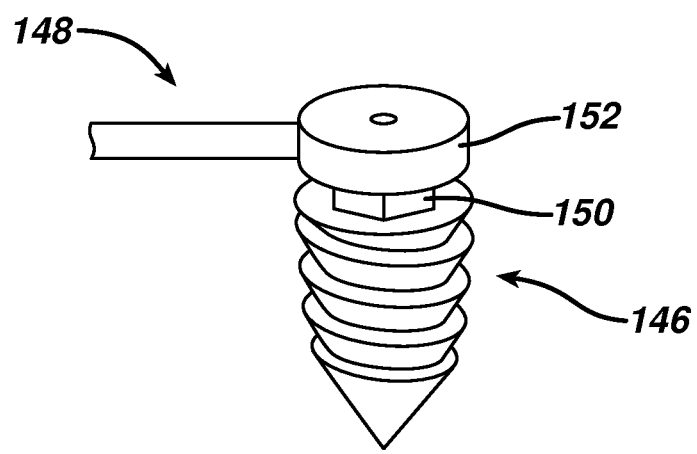
FIG. 18 is a side elevation view of a fifth embodiment of an instrument set according to the present invention in which a driver provides torque to a suture anchor laterally rather than axially.

FIG. 18 illustrates another alternative for engaging a threaded anchor 146 and a driver 148 having an anchor engagement 150, such as a hex head, which engages the anchor 146 from the side rather than axially. For an open procedure the driver could have a simple ratchet mechanism 152 to allow it to apply torque to the anchor 146 through the engagement 150 and cause it to spiral into bone beneath a tendon. The driver 142 could then be used for downward force and would not have to supply rotational force. For arthroscopic procedures it would be preferred to have an electric drive in which a rotating shaft engages a worm gear or similar gear connected to the engagement 150 to translate the rotation into the proper axis for rotating the anchor 146. Other drive mechanisms could include a chain and sprocket or belt drive.

Various modifications and alterations of this invention will be apparent to those skilled in the art without departing from the scope and spirit of this invention. It should be understood that the invention is not limited to the embodiments disclosed herein, and that the claims should be interpreted as broadly as the prior art allows. For instance, alternative grasper designs may be employed such as where a distal tip thereof fits into a hole in the anchor and is held by friction, snap-fit, temporary adhesive, threading, frangible connection, magnetism or the like. Such enhancements can be employed with other graspers. Further, the anchor can have indentations or flats on its outer surface to more easily allow grasping by a jaw-type grasper or snap-fit external grasper such as in FIG. 15B etc.

What is claimed is:
1. A method of attaching a partially torn rotator cuff tendon to its associated humeral head, the method comprising the steps of:
  passing a postional guid through the tendon toward the humeral head at a target site;
  positioning a suture anchor between the humeral head and the tendon at the target site by passing the suture anchor laterally under the tendon;
  driving the suture anchor into the humeral head; and
  passing suture from the suture anchor and through the tendon to attach the tendon to the humeral head at the target site; and
wherein the suture anchor comprises a first portion and a second portion which can assemble with each other and wherein the step of positioning the suture anchor at the target site comprises the steps of passing the first portion and the second portion in a disassembled state laterally under the tendon and then assembling the first portion to the second portion around the positional guide.

2. A method according to claim 1 wherein the positional guide is engaged with the humeral head during the step of assembling the first portion to the second portion.

3. A method of attaching a partially torn rotator cuff tendon to its associated humeral head, the method comprising the steps of:

passing a positional guide through the tendon toward the humeral head at a target site; passing an awl head laterally under the tendon to the target site and engaging the awl head against the humeral head via the positional guide;

positioning a suture anchor between the humeral head and the tendon at the target site by passing the suture anchor laterally under the tendon;

driving the suture anchor into the humeral head; and passing suture from the suture anchor and through the tendon to attach the tendon to the humeral head at the target site.

4. A method according to claim 3 and further comprising the step of driving the awl head into the humeral head to create a bone hole.

5. A method according to claim 4 and wherein the step of driving the suture anchor into the humeral head comprises inserting the suture anchor into the bone hole.

6. A method of attaching a partially torn rotator cuff tendon to its associated humeral head, the method comprising the steps of: passing a positional guide through the tendon toward the humeral head at a target site; passing an awl head laterally under the tendon to the target site and engaging the awl head against the humeral head via the positional guide; driving the awl head into the humeral head to create a bone hole; positioning a suture anchor between the humeral head and the tendon at the target site by passing the suture anchor laterally under the tendon; driving the suture anchor into the bone hole in the humeral head; and passing suture from the suture anchor and through the tendon to attach the tendon to the humeral head at the target site; and wherein the positional guide comprises a threaded distal tip and wherein the step of driving the awl head into the humeral head comprises engaging the awl head with the threaded distal tip of the positional guide, impacting the awl head via the positional guide to create the bone hole and then disengaging the awl head from the positional guide by unthreading the positional guide therefrom.

* * * * *